United States Patent [19]

Jensen

[11] 4,167,564

[45] Sep. 11, 1979

[54] BIOLOGICAL ASSIMILATION OF METALS

[75] Inventor: Ned L. Jensen, Clearfield, Utah

[73] Assignee: Albion Laboratories, Inc., Clearfield, Utah

[21] Appl. No.: 508,067

[22] Filed: Sep. 23, 1974

[51] Int. Cl.$^2$ .................. A61K 37/00; A61K 31/555; A61K 31/28; A61K 31/315

[52] U.S. Cl. ..................................... 424/177; 424/245; 424/287; 424/289; 424/294; 424/295; 424/319

[58] Field of Search .............. 424/294, 289, 295, 287, 424/319, 177, 245

[56] References Cited

U.S. PATENT DOCUMENTS

| | | | |
|---|---|---|---|
| 2,982,690 | 5/1961 | Ratcliff | 424/295 |
| 3,168,541 | 2/1965 | Hobbs | 424/295 |
| 3,367,834 | 2/1968 | Dexter | 424/295 |
| 3,463,858 | 8/1969 | Anderson | 424/289 |
| 3,466,312 | 9/1969 | Ercoli | 424/295 |

FOREIGN PATENT DOCUMENTS

868321  5/1961  United Kingdom ...................... 424/295

OTHER PUBLICATIONS

Miller Pharmacal Co., International Surgery Official Journal of the International College of Surgeons, Nov. 1971.

Chaberek and Martell, Organic Sequestering Agents, John Wiley & Sons, Inc., New York (1959), pp. 198–199; 203; 494–495.

Kirk–Othmer, Encyclopedia of Chemical Technology, vol. 6, pp. 14–18; 21–24 (1965).

Primary Examiner—Frederick E. Waddell
Attorney, Agent, or Firm—Criddle, Thorpe & Western

[57] ABSTRACT

A method for improving the stability of amino acid-metal complexes or chelates and enhancing the uptake of these complexes into biological tissues. This method comprises forming the metal complexes with amino acids or hydrolyzed proteins and incorporating into them a buffer system which controls the pH of the complex and its surrounding media. This uptake is accomplished by the system of amino acid active transport into the blood stream from which the complex is then carried throughout the entire body.

16 Claims, No Drawings

BIOLOGICAL ASSIMILATION OF METALS

BACKGROUND

The rate of growth and well-being of a living organism is dependent upon the ability and rate at which that organism is able to assimilate life's building blocks, i.e., proteins, carbohydrates, lipids, minerals and vitamins and convert or metabolize them into useful products for that organism. It is well known that many metals are essential to the proper functioning of a living organism. It is also well known that some metals are very difficult to assimilate into the cells of a living organism and are, for that reason, available in various forms, i.e., usually various organic and inorganic salts.

DESCRIPTION OF THE INVENTION

It has now been found that metabolically essential metals and trace elements such as iron, copper, zinc, manganese, cobalt, chromium, calcium, magnesium, vanadium and the like can be assimilated into a living organism if they are made available to that organism in the form of chelated coordination complexes with amino acids and other hydrolysis products of proteins in a buffered state at a relatively constant pH. For purposes of this disclosure, a chelate is defined to mean a coordination complex between the metal ion and an organic compound which is an amino acid or other organic compound derived from hydrolyzed protein and in which atoms within the organic compound are coordinated with the metal ion. Since proteins are made up of amino acids, the chelated coordination complex thus formed will hereinafter be referred to as a proteinate of the metal ion or a metal proteinate. Such terms shall be inclusive of coordination complexes with amino acids, proteins and proteins in any state of hydrolysis.

Any of the amino acids produced from proteins by hydrolysis are applicable to this invention. Most proteins yield about twenty different amino acids. These are all alpha amino acids and are listed as follows: glycine, alanine, valine, leucine, isoleucine, phenylalanine, tyrosine, tryptophan, serine, threonine, aspartic acid, glutamic acid, lysine, arginine, histidine, cystine, cysteine, methionine, proline and hydroxyproline. Preferred of the above amino acids are methionine, glycine, aspartic acid and glutamic acid. Especially preferred is methionine.

The buffer system functions to control the pH of the metal proteinate and its surrounding media and maintain it at a relatively constant state. By thus creating optimum conditions, the uptake or assimilation of metal proteinate into the surrounding tissues is hastened. For purposes of this application, it is irrelevant at which portion along the digestive tract the assimilation of the metal proteinate occurs. As will be seen in the following examples, the essential metal is rapidly distributed throughout the body tissues. The buffer system may change according to the metal proteinate being administered, and one or more metal proteinates may be administered at one time.

The choice of buffer system will depend upon the pH desired. The amino acids alone will interact with both acidic and basic solutions such as hydrocholoric acid (HCl) and sodium hydroxide (NaOH) to form buffered systems. Typical buffer solutions include acid phthalates, neutralized phthalates, phosphates, carbonates and bicarbonates and combinations thereof. Either alkali or alkaline earth metals may be utilized in the buffer system. Examples of buffering systems in the pH range of 3 to 11 are set forth below:

| pH | BUFFERS |
|---|---|
| 3.0 | 50 ml M/5 KHPhthalate + 22.3 ml M/5 HCl diluted to 200 ml |
| 4.0 | 50 ml M/5 KHPhthalate + 0.1 ml M/5 HCl diluted to 200 ml |
| 5.0 | 50 ml M/5 KHPhthalate + 22.6 ml M/5 NaOH diluted to 200 ml |
| 6.0 | 50 ml M/5 $KH_2PO_4$ + 5.6 ml M/5 NaOH diluted to 200 ml |
| 7.0 | 50 ml M/5 $KH_2PO_4$ + 22.4 ml M/5 NaOH diluted to 200 ml |
| 8.0 | 50 ml M/5 $KH_2PO_4$ + 46.1 ml M/5 NaOH diluted to 200 ml |
| 6.0 | 23.2g $KH_2PO_4$ + 4.3g $Na_2HPO_4$ per liter |
| 7.0 | 9.1g $KH_2PO_4$ + 19.7g $Na_2HPO_4$ per liter |
| 10.0 | 6.5g $NaHCO_3$ + 13.2g $Na_2CO_3$ per liter |
| 11.0 | 11.4g $Na_2HPO_4$ + 19.7g $Na_3PO_4$ per liter |

Other systems which have been successfully used are the combination of proteins which have a tendency to keep solutions at pH 7 with metal chelates and vitamins including ascorbic acid (Vitamin C). The present invention encompasses any combination of organic or inorganic substituents which will buffer or maintain a system at a pH range of from about 3 to 11 with acidic ranges of from about 3 to 6.9 and basic range of about 7 to 11. There are numerous other buffering systems readily available to one with ordinary skill in the art and mere enumeration of them at this point would be meaningless. What is important to the invention is that a buffering system be selected which will not only stabilize a metal proteinate solution but be non toxic and assist in the assimilation of such metal proteinate into the living organism.

While the term "living organism" has been referred to throughout this disclosure, the invention is primarily intended for the treatment of warm-blooded animals. The dosage to be administered will, of course, be dependent upon the type of animal, i.e., species, size, weight, age, sex, etc. and the metal proteinate being administered. Dosage is not a critical function of this invention as it may be empirically determined by one with ordinary skill in the art once the invention is defined. The method of dosage may also vary. The metal proteinate may be administered orally by ingestion or by means of a stomach tube. It may also be given by injection intramuscularly, intravenously or subcutaneously. If desired, the proteinate may be injected directly into any portion of the gastrointestinal tract by any appropriate means. When given to pregnant animals it has also been found that the buffered proteinates are sufficiently stable that they are transported across the placental barrier to the fetus. What is critical is the discovery that the uptake of essential metal can be enhanced by the use of the stabilized buffered metal proteinate complexes of this invention.

In order to demonstrate the improved assimilation of metal ions as metal proteinates into living tissue, several studies were undertaken utilizing radio isotopes. These metals were so tagged in order to quantitatively measure their uptake into the living organism.

The following examples are illustrative of the invention and are not to be construed as limitations thereon.

EXAMPLE I

Traces of $Zn^{65}Cl_2$ were mixed with non radioactive zinc chloride and complexed with methionine as an amino acid. To demonstrate structure and how tightly the methionine was bound to the zinc, a polarographic study was made. A solution was prepared containing 0.0001 moles of zinc per 100 mls of solution of $ZnCl_2$, and there was added thereto sufficient 0.2 M methionine to produce a solution having a molar ratio of amino acid to zinc as follows:

| Solution | Mls of 0.2M Methionine | Moles Ratio Methionine Zinc |
|---|---|---|
| 1 | 0 ml | 0 |
| 2 | 2.5 ml | 0.5 |
| 3 | 5.0 ml | 1.0 |
| 4 | 10.0 ml | 2.0 |
| 5 | 20.0 ml | 4.0 |
| 6 | 40.0 ml | 8.0 |
| 7 | 80.0 ml | 16.0 |

To each of the above solutions was added 10 mls of 1 M potassium nitrate ($KNO_3$) as an electrolyte and 10 mls of a 0.1% gelatin solution. Each solution was corrected to a pH of 7 by the addition of a few drops of concentrated (6 N) sodium hydroxide (NaOH) solution.

Using a Metrohm E 261 polarograph with a silver/silver chloride (Ag/AgCl) reference electrode, the following $E_{1/2}$'s were recorded:

| Solution No. | $E_{\frac{1}{2}}$ |
|---|---|
| 1 | −1.008 |
| 2 | −1.033 |
| 3 | −1.057 |
| 4 | −1.079 |
| 5 | −1.090 |
| 6 | −1.110 |
| 7 | −1.129 |

A plot of the log of the proteinate ligand concentration against the $E_{1/2}$ gives a sloped line which is indicative of the number of ligands in the complex. It was found that the $Zn^{++}$ ion complexes with two molecules of methionine.

While not wishing to be bound by any specific theory, it is believed that at higher ligand concentrations and at a higher pH (more basic) the complex is probably a bicyclic complex.

By knowing the number of ligands, the stability constant at different concentrations and pH's can be determined. It has been found that the logarithm of the stability constant equals:

$$\log K = \frac{2}{.059} \left[ E_{1/2} - p \log [\text{ligand}] \frac{.059}{2} \right]$$

where p=the number of ligands and [ligand] refers to the concentration of the ligand.

Solution Number 7 (16 moles of methionine per mole of zinc) was found to have a stability constant equal to $4.94 \times 10^7$ at pH 7. The same solution was adjusted to a pH of 9 and the stability constant was found to be $4.41 \times 10^{12}$. In other words, by changing the pH of a zinc methionate solution of the same concentration from 7 to 9 an increase in stability of $10^5$ or 100,000 was obtained. Similar results can be demonstrated with copper, iron, chromium, calcium, manganese, magnesium, vanadium and other essential metals.

EXAMPLE II

The following study was done to correlate the results obtained in Example I with the way animals absorb the buffered metal proteinate complexes. White laboratory rats were used as experimental animals, and each rat received the same amount of tagged zinc chloride by dosing with a pipette directly into the rat's stomach. The molar ratio of zinc to methionine was one to two for Rat II and III, and the pH was adjusted according to the following table:

| Rat I | Rat II | Rat III |
|---|---|---|
| 24 microliters $Zn^{65}Cl_2$ | 24 microliters $Zn^{65}Cl_2$ | 24 microliters $Zn^{65}Cl_2$ |
| 75 microliters $H_2O$ | 25 microliters $H_2O$ containing $NaHCO_3/Na_2CO_3$ to pH 10 | 25 microliters $H_2O$ containing NaOH to pH 7 |
| | 50 microliters methionine-solition 2:1 molar ratio with $Zn^{++}$ | 50 microliters methionine-solution 2:1 molar ratio with $Zn^{++}$ |

The rats were placed in metabolic cages on a normal diet and were observed for one week during which time the feces were collected. At the end of the week, the rats were sacrificed, and the total excreta measured by scintillation count for radioactivity as compared to a blank. The following amounts of $Zn^{++65}$ were excreted by each of the rats as measured by the collected feces for the week:

| % of Total Dose Excreted | |
|---|---|
| Rat I | 52% |
| Rat II | 12% |
| Rat III | 36% |

More than half of the $Zn^{65}Cl_2$ in the control animal was lost. The $Zn^{65}$ methionate retention in Rat II administered at pH 10 was significantly better than the $Zn^{65}$ methionate retention in Rat III administered at pH 7. However, both showed marked improvement in $Zn^{++}$ retention over Rat I.

EXAMPLE III

Example II was essentially repeated using $Fe^{59}SO_4$ as the control. The solution was orally administered by pipette into the stomach. Each rat received 36.7 micrograms of $Fe^{59}$ in 20 microliters of sollution. Rat II was administered a methionine solution and Rat III a glycine solution, both buffered to a pH of 10 in a molar ratio of two to one metal to amino acid. At the end of a week, the rats were sacrificed and parts of various organs analyzed for $Fe^{++59}$ by scintillation count.

The following results were obtained:

| Tissue | CORRECTED COUNTS PER MINUTE PER GRAM | | |
|---|---|---|---|
| | Rat I FeSO$_4$ | Rat II FeMet | Rat III FeGly |
| Heart | 63. | 151. | 83. |
| Liver | 136. | 243. | 83. |
| Gastroc | 2. | 54. | 83. |
| Masseter | 14. | 138. | 65. |
| Brain | 31. | 130. | 142. |
| Kidney | 2. | 327. | 150. |
| Testes | 20. | 109. | 75. |
| Serum | 700. | 1,797. | 840. |
| Cells | 742. | 2,076. | 773. |
| Blood | 1,335. | 4,215 | 1,602. |
| Feces | 302,400. | 314,000. | 205,800. |
| Urine | 490. | 370. | 690. |
| | Rat I | Rat II | Rat III |
| Feces | 45.8% Lost | 32.4% Lost | 31.2% Lost |

The results reported above are very dramatic. The amounts of $Fe^{++59}$ retained by Rats II and III administered the buffered $Fe^{59}$ proteinate were significantly higher than in Rat I as demonstrated by the feces analysis. The amounts of metal retained in the tissues were also significantly higher in almost every instance. However, detailed results were not computable because the complete organ was not removed for analysis.

Buffering systems which were used in the above examples include amino acid-NaOH solutions and a solution of 6.5 grams of sodium bicarbonate (NaHCO$_3$) and 13.2 grams of sodium carbonate (Na$_2$CO$_3$) per liter of solution which will produce a buffered solution of about pH 10.

EXAMPLE IV

To further substantiate the effects of buffering metal proteinates, the following tests were conducted on rats which had been fasted over night. Each rat was given the following dosage of radioactive calcium by injection into the duodenum:

Rat I
  250 microliters of CaCl$_2$ solution (1 mg. Ca) is distilled H$_2$O
  40 microliters of distilled H$_2$O (40 mcC Ca$^{45}$)* as Ca$^{45}$Cl$_2$
*mcC=micro curies Rat II
  250 microliters of CaCl$_2$ solution (1 mg Ca) in distilled H$_2$O buffered to pH 7 with NaOH and the amino acids and containing in molar ratio with calcium 2 moles of aspartic acid, 2 moles of glycine and 1 mole of methionine
  40 microliters of distilled H$_2$O (40 mcC Ca$^{45}$) as Ca$^{45}$Cl$_2$ Rat III
  Same as Rat II except buffered to Ph 10 with NaHCO$_3$/Na$_2$CO$_3$.

The rats were fed a normal diet for one week, and the feces were collected. At the end of one week the rats were sacrificed and the total feces and portions of the tissues were analyzed by scintillation count. The results obtained are as follow:

| Tissues | CORRECTED COUNTS PER MINUTE PER GRAM | | |
|---|---|---|---|
| | Rat I | Rat II | Rat III |
| Frontal Bone | 3682 | 5878 | 5772 |
| Massater | 602 | 844 | 904 |
| Gastroc (muscle) | 614 | 620 | 1206 |
| Heart | 642 | 598 | 932 |
| Liver | 664 | 546 | 742 |
| R. Cerebrum | 698 | 726 | 804 |
| Kidney | 686 | 656 | 730 |
| Lung | 676 | 672 | 648 |
| Serum } 100 microliters | 8.4 | 39.6 | 31.0 |
| Cells } Blood | 18.6 | 0 | 13.2 |
| Total Blood | 27.0 | 39.6 | 44.2 |

It is evident from the tissue counts that much more of the calcium proteinate was assimilated into the tissues at the buffered Ph of 10 than at pH 7. However, it is also evident that more of the calcium proteinate was absorbed at the buffered pH 7 than was the calcium salt control.

Insofar as the feces is concerned, it can readily be seen that about four times as much calcium was excreted in the simple organic salt control (Rat I) than in the buffered (pH 10) calcium proteinate. Moreover, the pH 10 proteinate was approximately twice as effective in retaining calcium than was the buffered (pH 7) proteinate. It would thus appear that buffering undoubtedly assists in both promoting stability of the metal proteinate solution and in improving its assimilation into a host of various tissues.

EXAMPLE V

The above examples tend to show that a buffer system at about pH 10 will improve certain metal assimilation into living tissues. This pH however is not optimum for all metals. Some metals actually are better absorbed at a lower (more acidic) buffered range. The object is to find and maintain the optimum pH range for the metal to be administered. This may be empirically established for each metal proteinate.

Manganese, for example, is absorbed better as a proteinate at lower pH's than in more basic systems where it tends to form Mn(OH)$_2$.

Manganese, calcium also do not function well with carbonate buffered solutions in that they tend to form insoluble carbonates.

The absorptive capacities of manganese proteinates at a buffered pH of 7 are demonstrated below. Two solutions utilizing Mn$^{54}$ were made up as follows:

Solution I
  250 microliters distilled H$_2$O containing 100 mg of Mn as MnCl$_2$
  20 microliters Mn$^{54}$ solution (14.3 mcC) (Slightly acidic pH) as Mn$^{54}$Cl$_2$ Solution II
  250 microliters distilled H$_2$O containing 100 mg of Mn as MnCl$_2$
  20 microliters Mn$^{54}$ solution (14.3 mcC) as Mn$^{54}$Cl$_2$
  Based on a molar ratio of total manganese, the solution contained per mole of manganese, 2 moles each of the amino acids—methionine, glycine, aspartic acid and glutamic acid. The solution was buffered to a pH 7 with NaOH interacting with the amino acids.

The solutions prepared were injected into the duodenum of laboratory rats (labeled Rat I and Rat II according to solution given) which were fed a normal diet for one week and then sacrificed. The tissues were then measured by scintillation count as an indication of manganese proteinate uptake. The results are as follows:

biological tissues measured for radio active iron by scintillation count. Measurements were also made of the hemoglobin and hematocrit of the mother and the kits. The data obtained are given in the two following tables.

| GENERAL DATA | | |
| --- | --- | --- |
| | Mink No. 1 | Mink No. 2 |
| Total % $Fe^{++}$ Retained | 70.4 | 42.7 |
| Total % $Fe^{++}$ Excreted in feces | 24.4 | 29.6 |
| Total % $Fe^{++}$ Excreted in urine | 5.17 | 27.7 |
| % $Fe^{++}$ Excreted in Feces 4 days after dosing | 21.5 | 23.8 |
| % $Fe^{++}$ Passed on to young (kits) | 0.03 (7.3 micrograms) | 0 |
| Hemoglobin Mother-gm % | 20.5 | 20.0 |
| Hematocrit % | 45 | 44 |
| Average Hemoglobin of young (kits) gm/% | 19.5 | 19 |
| Average Hematocrit of young (kits) | 53 | 50 |
| Whole Body Counts Without Organs Mother (corrected counts/minute) | 112.4 | 68.1 |
| Average Body Counts Per Kit (Corrected Counts/minute) | 42.3 | 1 |

| CORRECTED COUNTS PER MINUTE PER GRAM | | |
| --- | --- | --- |
| | cc/min/gm dry wt | |
| | I | II |
| Heart | 370 | 1190 |
| Kidney | 470 | 600 |
| Brain | 620 | 1170 |
| Gastroc | 800 | 660 |
| Masseter | 270 | 310 |
| Liver | 760 | 1070 |
| Lung | 720 | 330 |
| Frontal Bone | 350 | 780 |
| Duodenum | 170 | 480 |

| CORRECTED COUNTS PER MINUTE PER GRAM | | |
| --- | --- | --- |
| Tissue | Mink No. 1 | Mink No. 2 |
| Masseter | 7.81 | 12.00 |
| Pectoralis Major | 1.22 | 5.02 |
| Spleen | 15.3 | 10.60 |
| Brain | 9.7 | 7.57 |
| Lung | 6.4 | 4.05 |
| Heart | 2.7 | 5.12 |
| Liver | 4.98 | 4.73 |
| Neck Fur and Skin | 6.24 | 3.82 |
| Scalp | 5.74 | 6.33 |

As will be noted from the above table, almost all counts were higher in Rat II administered the manganese proteinate than in control Rat I. Counts in urine and feces from these animals were not obtained.

EXAMPLE VI

The above examples illustrate the assimilation of buffered metal chelate complexes with isolated amino acids or limited combinations of acids. This example demonstrates that hydrolized protein (containing essentially all the amino acids) may be used as effectively. This example further demonstrates the placental transfer of stabilized metal proteinates from the mother to the unborn fetus. Mink were chosen for these tests and iron was chosen for the metal proteinate. This was done because many authorities in mink production believe that mink have difficulty in placental transfer of iron from mother to young.

Two pregnant mink individually housed were fasted for twenty to twenty-four hours and were then given 24.17 milligrams of iron containing 5 mcC of $Fe^{59}$ ratio active isotope. Mink No. 1 was given the iron in the form of $Fe^{59}SO_4$ which had been chelated into hydrolyzed protein and buffered with a $NaHCO_3/Na_2CO_3$ solution to a pH of 10. Mink No. 2 was given the same amount of iron as $Fe^{59}SO_4$. In each case, the isotopes were mixed with 25 grams of food which was consumed by the mink by ingestion. The iron was administered to each mink 15 days before whelping. Faces and urine from each mink were collected to determine the amount of $Fe^{++}$ excreted. Measurements were recorded 4 days after dosing and at the time of sacrifice. Fifteen days after dosing each mink was sacrificed and the various From the above data several conclusions can be drawn. It is at once evident that the amount of $Fe^{++}$ retained in Mink No. 1, dosed with the buffered iron proteinate was 65% greater than the amount retained in Mink No. 2 dosed with $Fe_2SO_4$. Stating it another way about 70% of the iron in the buffered iron proteinate was metabolized whereas only 42.7% was retained in the mink treated with $Fe_2SO_4$.

Comparing the amounts of iron excreted after 4 days with the final analysis, it is evident that in Mink No. 2 33.5% of the iron initially dosed was absorbed but not metabolized, and was eventually eliminated between the fourth and fifteenth day after dosing. In Mink No. 1 only about 8% of the absorbed iron proteinate was later eliminated and not metabolized. The data show that a measurable amount of $Fe^{++}$ as iron proteinate was carried to the kits from Mink No. 1 by placental transfer (42.3 cc/min) whereas the $Fe^{++59}$ in the kits from Mink No. 2 was barely evident (1 cc/min). The hemoglobin and hematocrit measurements were higher from the iron proteinate dosed mink than from the control. The iron proteinate is utilized in the blood, skin and organs more readily as shown by tissue counts. The spleen, which is 90% blood, contains about 50% more iron from the buffered iron proteinate than from the $Fe_2SO_4$ control. This is important as it demonstrates that the iron proteinate is better for building hemoglobin than the corresponding $Fe_2SO_4$. Finally, the data show that hydrolyzed protein is as effective a ligand for complexing with buffered metals to form metal proteinates for transport of metal into the blood stream from the intestinal tract as the individual amino acids.

I claim:

1. A stabilized metal proteinate for enhancing the uptake of essential minerals into warm blooded animals comprising a metal coordination complex between a metal ion selected from the group consisting of iron, copper, zinc, manganese, cobalt, chromium, calcium, magnesium and vanadium, and an amino acid selected from group consisting of glycine, alanine, valine, leucine, isoleucine, phenylalanine, tyrosine, tryptophan, serine, threonine, aspartic acid, glutamic acid, lysine, arginine, histidine, cystine, cysteine, methionine, proline, hydroxyproline and mixtures thereof, the proteins made up from said amino acids and hydrolysis products of such proteins in a molar ratio of between two and sixteen moles of amino acid, protein or hydrolyzed protein per mole of metal, said metal being stabilized by a buffering system comprising a member or members selected from the group consisting of amino acid-hydrochloric acid mixtures, or amino acid-sodium hydroxide mixtures and mixtures of alkali or alkaline earth metal salts of acid phthalates, neutralized phthalates, acid phosphates and acid carbonates with hydrochloric acid, sodium hydroxide and alkali or alkaline earth metal salts of acid phosphates, phosphates and carbonates, wherein the buffering system maintains the metal proteinate at a relatively constant pH between about 7 and 11.

2. A stabilized metal proteinate according to claim 1 wherein the proteinate is an amino acid selected from the group consisting of glycine, alanine, valine, leucine, isoleucine, phenylalanine, tyrosine, tryptophan, serine, threonine, aspartic acid, glutamic acid, lysine, arginine, histidine, cytine, cysteine, methionine, proline, hydroxyproline and mixtures thereof.

3. A stabilized metal proteinate according to claim 2 wherein the amino acid is selected from the group consisting of methionine, glycine, aspartic acid, glutamic acid and mixtures thereof.

4. A stabilized metal proteinate according to claim 3 wherein the amino acid is methionine.

5. A stabilized metal proteinate according to claim 1 wherein the proteinate is a hydrolyzed protein.

6. A stabilized metal proteinate according to claim 1, wherein the buffer system is a combination of sodium bicarbonate and sodium carbonate.

7. A stabilized metal proteinate according to claim 1 wherein the buffer system is an amino acid-sodium hydroxide solution.

8. A method of aiding in the assimilation of essential metals into warm blooded animals which comprises administering to said warm blooded animals an effective amount of an aqueous solution of a stabilized metal proteinate comprising a metal coordination complex between a metal ion selected from the group consisting of iron, copper, zinc, manganese, cobalt, chromium, calcium, magnesium and vanadium, and an amino acid selected from group consisting of glycine, alanine, valine, leucine, isoleucine, phenylalanine, tyrosine, tryptophan, serine, threonine, aspartic acid, glutamic acid, lysine, arginine, histidine, cystine, cysteine, methionine, proline, hydroxyproline and mixtures thereof; the proteins made up from said amino acids and hydrolysis products of such proteins in a molar ratio of between two and sixteen moles of amino acid, protein or hydrolyzed protein per mole of metal, said metal being stabilized by a buffering system comprising a member or members selected from the group consisting of amino acid-hydrochloric acid mixtures, or amino acid-sodium hydroxide mixtures and mixtures of alkali or alkaline earth metal salts of acid phthalates, neutralized phthalates, acid phosphates and acid carbonates with hydrochloric acid, sodium hydroxide and alkali or alkaline earth metal salts of acid phosphates, phosphates and carbonates, wherein the buffered system maintains the metal proteinate at a relatively constant pH between 7 and 11.

9. A method according to claim 8, wherein said buffered metal proteinate is administered orally.

10. A method according to claim 9 wherein said living organism is a warm-blooded animal.

11. A method according to claim 9 wherein the metal is a member selected from the group consisting of iron, copper, zinc, manganese, cobalt, chromium, calcium, magnesium and vanadium and is complexed with a proteinate which is an amino acid selected from the group consisting of glycine, alanine, valine, leucine, isoleucine, phenylalanine, tyrosine, tryptophan, serine, threonine, aspartic acid, glutamic acid, lysine, arginine, histidine, cystine, cysteine, methionine, proline, hydroxyproline and mixtures thereof.

12. A method according to claim 11 wherein the amino acid is selected from the group consisting of methionine, glycine, aspartic acid, glutamic acid and mixtures thereof.

13. A method according to claim 12 wherein the amino acid is methionine.

14. A method according to claim 8 wherein the proteinate is a hydrolyzed protein.

15. A method according to claim 8 wherein the buffer is a mixture of sodium carbonate and sodium bicarbonate.

16. A method according to claim 8 wherein the buffer is an amino acid-sodium hydroxide system.

* * * * *